US00PP13804P29

(12) United States Plant Patent
Drewlow

(10) Patent No.: US PP13,804 P2
(45) Date of Patent: May 13, 2003

(54) POINSETTIA PLANT NAMED 'FESTIVAL WHITE'

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 10/174,062

(22) Filed: Jun. 18, 2002

(51) Int. Cl.[7] ..... A01H 5/00

(52) U.S. Cl. ..... Plt./304
(58) Field of Search ..... Plt./304

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Festival White', characterized by its uniform plant growth habit; dark green-colored leaves with green-colored petioles; early flowering habit; inflorescences with white-colored flower bracts; and excellent post-production longevity.

1 Drawing Sheet

BOTANICAL CLASSIFICATION/CULTIVAR DENOMINATION

*Euphorbia pulcherrima* Willd. cultivar Festival White.

BACKGROUND OF THE INVENTION

The present Invention relates to a new and distinct cultivar of Poinsettia plant, botanically known as *Euphorbia pulcherrima* Willd., and hereinafter referred to by the name 'Festival White'.

The new Poinsettia is a product of a planned breeding program conducted by the Inventor in Lompoc, Calif. The objective of the breeding program is to create new Poinsettia cultivars with uniform plant habit and attractive flower bract coloration.

The new Poinsettia is a induced mutation of the *Euphorbia pulcherrima* Willd. cultivar Festival Pink, not patented. The new Poinsettia was discovered and selected by the Inventor as a single plant within a population of irradiated plants of the cultivar Festival Pink in a controlled environment in Lompoc, Calif. The selection of this plant was based on its attractive flower bract coloration and uniform plant habit.

Asexual reproduction of the new Poinsettia by vegetative terminal cuttings taken at Lompoc, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Festival White'. These characteristics in combination distinguish 'Festival White'as a new and distinct cultivar:

1. Uniform plant growth habit.
2. Dark green-colored leaves with green-colored petioles.
3. Early flowering habit.
4. Inflorescences with white-colored flower bracts.
5. Excellent post-production longevity.

Plants of the new Poinsettia differ primarily from plants of the parent cultivar in flower bract coloration as plants of the cultivar Festival Pink have pink-colored flower bracts.

Plants of the new Poinsettia can be compared to plants of the cultivar 490 White, disclosed in U.S. Plant Pat. No. 8,772. In side-by-side comparisons conducted in Lompoc, Calif., plants of the new Poinsettia differed from plants of the cultivar 490 White in the following characteristics:

1. Plants of the new Poinsettia were more upright and not as outwardly spreading as plants of the cultivar 490 White.
2. Plants of the new Poinsettia had reddish-colored stems whereas plants of the cultivar 490 White had green-colored stems.
3. Plants of the new Poinsettia had smaller leaves and shorter petioles than plants of the cultivar 490 White.
4. Plants of the new Poinsettia had tighter cyathia clusters than plants of the cultivar 490 White.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a top perspective view of a single flowering plant of 'Festival White' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photograph and, following observations and measurements describe plants grown in Lompoc, Calif. during the fall and winter under commercial practice in a fiberglass-covered greenhouse with night temperatures about 16° C. and light levels about 3,000 to 4,000 foot-candles. Single plants were grown in 15-cm pots, pinched once, and flowered under controlled short day/long night conditions. Plants were about 17 weeks from unrooted cuttings when the photographs and the detailed botanical description were taken.

In the following description, color references are made to The Royal Horticultural Society Colour Chart, 1995 edition, except where general terms of ordinary dictionary significance are used.

Botanical classification: *Euphorbia pulcherrima* Willd. cultivar Festival White.

Parentage: Induced mutation of the *Euphorbia pulcherrima* Willd. cultivar Festival Pink, not patented.

Propagation:

*Type cutting.*—Vegetative terminal cuttings.

*Time to produce rooted young plants.*—Summer: About 14 days at 21° C. Winter: About 18 days at 21° C.

*Root description.*—Thick, fibrous and freely-branching.

Plant description:

*Growth habit.*—Upright and uniform plant habit; inverted triangle; vigorous.

*Plant height.*—About 25 to 30 cm.

*Plant diameter or spread.*—About 40 to 45 cm.

*Lateral branch description.*—Quantity: Plants pinched to five to six leaves develop one lateral branch per node. Strength: Strong. Color: Close to 185D.

*Foliage description.*—Arrangement: Alternate, single. Length: About 10 to 11 cm. Width: About 7 to 8 cm. Shape: Ovate. Apex: Acuminate. Base: Acute to obtuse. Margin: Entire with irregular lobing. Venation pattern: Pinnate. Texture, upper and lower surfaces: Glabrous. Surface: Rugose. Color: Young foliage, upper surface: 146A. Young foliage, lower surface: 146B. Fully expanded foliage, upper and lower surfaces: 147A. Petioles: Length: About 5 to 6 cm. Texture: Glabrous. Color, upper and lower surfaces: 145C.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under short day/long night conditions. Early flowering; response time, about 7.5 weeks, under controlled photoperiod conditions.

*Post-production longevity.*—Plants of the new Poinsettia maintain good substance and bract color for about six to eight weeks under interior conditions.

*Quantity of inflorescences.*—One per lateral branch, about five or six per plant.

*Inflorescence diameter.*—About 30 to 35 cm.

*Flower bracts.*—Quantity of flower bracts: About 20 to 25 per inflorescence. Length, largest bracts: About 14 to 15 cm. Width, largest bracts: About 8 to 9 cm. Shape: Ovate. Apex: Acuminate. Base: Obtuse. Margin: Entire. Texture, upper and lower surfaces: Glabrous. Surface: Rugose. Orientation: Mostly horizontal. Color: Developing bracts, upper and lower surfaces: 158B. Fully developed bracts, upper and lower surfaces: 158C.

*Cyathia.*—Quantity of cyathia: About 10 to 15 per corymb. Diameter of cyathia cluster: About 3.5 to 4 cm. Shape: Ovoid. Color: 144B. Stamens: Quantity of stamens: At least ten per cyathium. Anther shape: Oblong. Anther color: 11A. Filament color: 11A. Pollen color: Close to 14A. Pistils: Quantity of pistils: One per cyathium. Style color: 154D. Stigma color: 154C. Ovaries: Quantity of ovaries: Three per cyathium. Color: 144A. Nectaries: Quantity of nectaries: One per cyathium. Color: Close to 12A.

Disease resistance: Plants of the new Poinsettia have been observed to be resistant to Botrytis.

It is claimed:

1. A new and distinct cultivar of Poinsettia plant named 'Festival White', as illustrated and described.

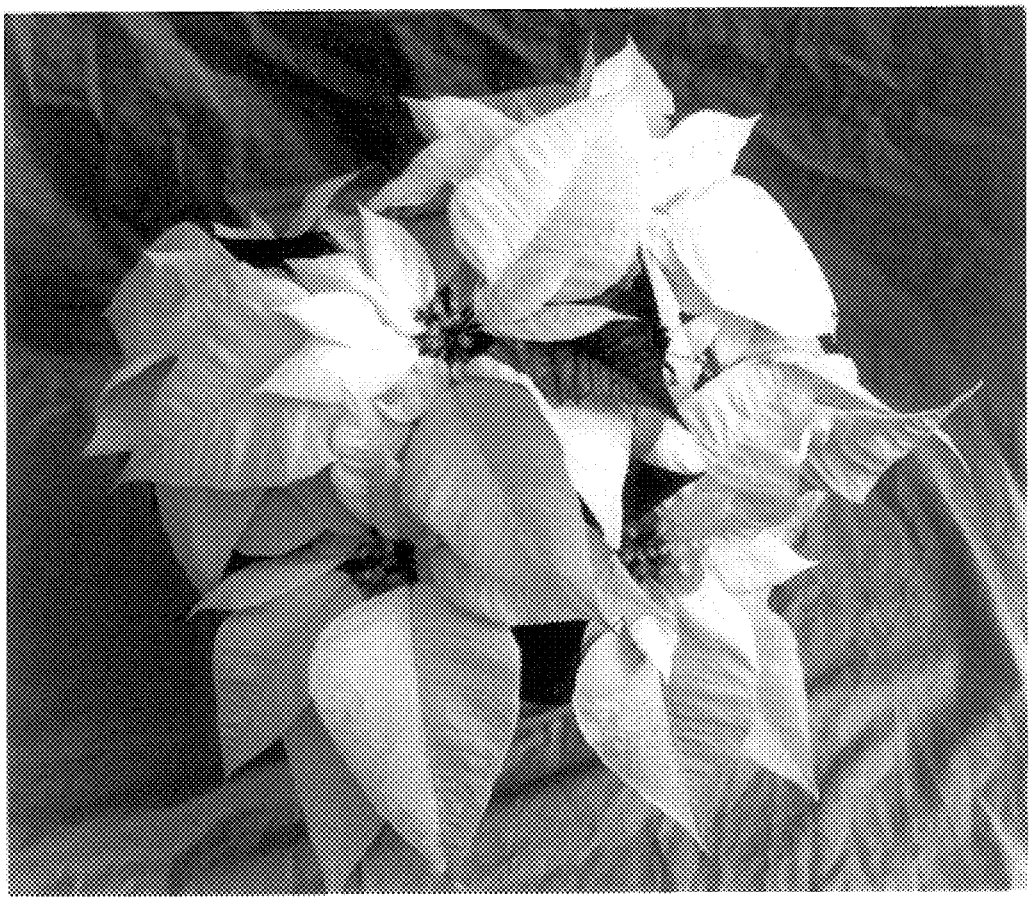

* * * * *